(12) United States Patent
Levy

(10) Patent No.: US 9,622,906 B2
(45) Date of Patent: Apr. 18, 2017

(54) COSMETIC AND DERMATOLOGICAL CRYOTHERAPY DEVICE

(76) Inventor: Elizabeth Joyce Levy, San Diego, CA (US)

( * ) Notice: Subject to any disclaimer, the term of this patent is extended or adjusted under 35 U.S.C. 154(b) by 1157 days.

(21) Appl. No.: 13/558,803

(22) Filed: Jul. 26, 2012

(65) Prior Publication Data

US 2012/0303104 A1    Nov. 29, 2012
US 2016/0228172 A9    Aug. 11, 2016

Related U.S. Application Data

(62) Division of application No. 12/830,397, filed on Jul. 23, 2010, now abandoned.

(60) Provisional application No. 61/233,480, filed on Aug. 12, 2009.

(51) Int. Cl.
   *A61F 7/10*    (2006.01)
   *A61F 7/00*    (2006.01)

(52) U.S. Cl.
   CPC .............. *A61F 7/10* (2013.01); *A61F 7/00* (2013.01); *A61F 2007/0052* (2013.01); *A61F 2007/0087* (2013.01); *A61F 2007/108* (2013.01)

(58) Field of Classification Search
   CPC combination set(s) only.
   See application file for complete search history.

(56) References Cited

U.S. PATENT DOCUMENTS

| | | | |
|---|---|---|---|
| 2,621,786 A | 12/1952 | Schnack | |
| 2,825,339 A * | 3/1958 | McGee | A61B 18/02 607/114 |
| 3,168,895 A | 2/1965 | Okuhata | |
| 4,240,436 A | 12/1980 | Singleton | |
| 4,243,041 A | 1/1981 | Paul | |
| 4,378,025 A * | 3/1983 | Gaston | A61K 8/02 424/401 |
| 4,404,820 A * | 9/1983 | Romaine | A61F 7/10 215/12.2 |
| 4,841,970 A * | 6/1989 | Rand | A61F 7/12 606/21 |
| 5,423,875 A | 6/1995 | Kehe | |
| 6,017,337 A | 1/2000 | Pira | |
| 6,185,742 B1 | 2/2001 | Doherty | |
| 6,245,093 B1 * | 6/2001 | Li | A61F 7/007 607/96 |
| 7,287,656 B2 | 10/2007 | Guilford, III et al. | |
| 7,832,225 B2 * | 11/2010 | Sanchez | A45D 34/04 132/320 |
| 2003/0125741 A1 * | 7/2003 | Biedermann | A61B 17/7032 606/278 |
| 2007/0186951 A1 * | 8/2007 | Gueret | A45D 34/00 132/320 |
| 2008/0141683 A1 | 6/2008 | O'Connor et al. | |

* cited by examiner

*Primary Examiner* — Joseph Stoklosa
*Assistant Examiner* — Adam Avigan
(74) *Attorney, Agent, or Firm* — George S. Levy

(57) ABSTRACT

A dermatological device for cooling the skin comprised of an ice pack and a heat conductive shield configured to operate as an aseptic separator between said skin and the ice pack and to conduct heat from the skin to the ice pack. This invention is also a method of cooling the skin which comprises cooling an ice pack, placing the ice pack over an aseptic shield and applying the other side of the shield to the skin. Heat flow is controlled by adjusting the contact surface between components within the shield.

19 Claims, 10 Drawing Sheets

COSMETIC AND DERMATOLOGICAL CRYOTHERAPY DEVICE

FIELD OF THE INVENTION

This invention is a divisional continuation of application Ser. No. 12/830,397. It claims the benefit of U.S. Provisional Application No. 61/233,480 with the title, "Cosmetic and Dermatological Skin Treatment Device" filed on Aug. 12, 2009 and which is hereby incorporated by reference. Applicant claims priority pursuant to 35 U.S.C. Par 119(e)(i). The present invention relates to cosmetic and dermatological devices and methods. More specifically it is concerned with the application of cold temperatures to the skin for therapeutic or cosmetic purposes, for example for the treatment of swelling and redness as is found in, but not limited to, acne.

U.S. Pat. No. 4,378,025 by Bontemps R. Gaston and U.S. Pat. No. 3,168,895 by Motoharu Okuhara are also incorporated by reference.

BACKGROUND

Acne vulgaris is a common dermatologic disorder with a high prevalence in teenagers and young adults, and especially in women. It consists of both inflammatory and non-inflammatory types of lesions; non-inflammatory lesions include open and closed comedones, while inflammatory lesions include papules, pustules, and cysts. Acne is widely believed to have a multi-factorial origin, and evidence suggests that elevated sebum secretion, follicular hyperkeratosis, bacterial proliferation (P. acnes) and inflammation may play roles to varying degrees. Other influences include sex hormones and psychological stressors. Current treatments of acne therefore focus on remedying one or more of these factors.

Cryotherapy, or short-term (approximately or less than 15 minutes) application of moderately cold temperature to the skin, is widely accepted as having an anti-inflammatory effect and has various applications in medicine. (This is to be distinguished from cryosurgery, which consists of locally applying extreme cold to an affected area with the intent of obliterating abnormal tissue.) Moderate cold temperature has been shown to cause localized vasoconstriction, decreased cellular permeability, decreased cellular metabolism, and to decelerate bacterial replication. These effects synergistically diminish the inflammatory biochemical cascade response to cellular injury.

U.S. Pat. No. 4,378,025 by Gaston R. Bontemps describes a cooling device in the form of deep-frozen blocks or cakes of cosmetic substances which are directly applicable to the skin. The vasoconstrictive action of the cold is added to the action of the cosmetic substance. Bontemps' invention, however, poses a risk to the user. If the blocks of cosmetics are frozen in a conventional household freezer, they may become contaminated with microorganisms from the freezer environment, which may infect the very sores that the user is treating. In addition, if the blocks are returned to the freezer after use, they may transfer organisms from the user to the food stored in the freezer. The cold temperature of the freezer would support the preservation of these contaminants for an extended period of time. In addition, since these frozen blocks cannot be easily cleaned after being applied to one sore, they may promote the transfer of microorganisms from one place on the skin to a different place or from one person to another.

This invention is not limited to the treatment of acne vulgaris; other ailments benefiting from localized cryotherapy as recognized by the medical art may also benefit from this invention.

This invention solves the problems identified above. None of the prior art offers the economy and hygiene of the present invention. Further features, aspects, and advantages of the present invention over the prior art will be more fully understood when considered with respect to the following detailed description and claims.

SUMMARY OF THE INVENTION

Figure 1:
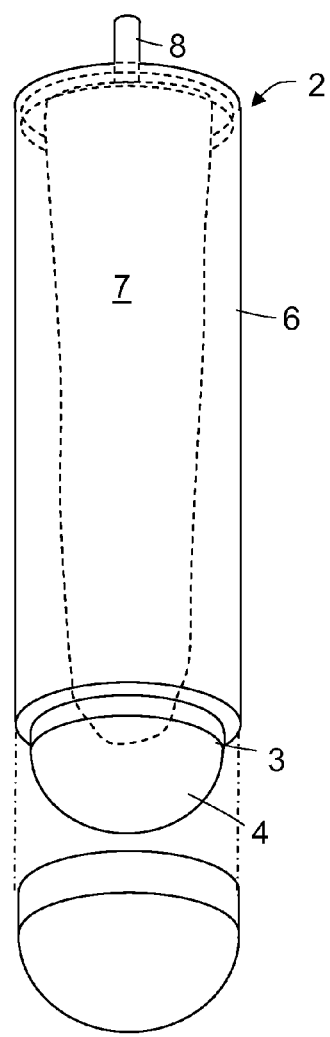
FIG. 1 is a perspective front view of the device.

This invention is a dermatological device for cooling of the skin. It comprises:
  a) An ice pack;
  b) A heat conductive shield configured to operate as an aseptic separator between the skin and the ice pack and to conduct heat from the skin to the ice pack.

In one particular embodiment of this invention, the shield is configured as a tube open at its back end and closed at its front end. The ice pack is shaped to snugly fit inside the tube.

Heat flow is optimized by building most of the tube in aluminum or copper.

As an option, and even though stainless steel does not conduct heat as well as aluminum or copper, a stainless steel cladding can be used to cover the tube's front end to facilitate cleaning and provide an increased degree of asepsis. As yet another option, the tube can also be completely built of stainless steel.

Heat flow can also be channeled away from the front toward the back by tapering the thickness of the tube, thick at the front and thin at the back and by covering it with a thermal insulating layer to avoid heat transfer except at the front tip.

A thermally insulating cap can also be employed to cover the front of the tube, thereby minimizing heat flow when the device is not in use.

The ice pack can either be soft-walled or be hard-walled. It can include a handle for its easy removal from, or insertion into, the tube. The chemicals held by the ice pack may include but are not limited to water, alcohol, ethylene glycol, and super absorbent polymers.

The shield can be configured to have controllable heat conductivity by adjusting the amount of contact surface between the icepack and the shield or between internal components in the shield itself. This can be done by means of a screw arrangement whereby the stainless steel cladding and the aluminum or copper material comprising the tube have a variable amount of common surface in contact with each other.

The method of using this invention includes cooling the ice pack in a freezer or refrigerator. The aseptic shield is then applied to the skin and the ice pack is placed in contact with the shield, thereby cooling the skin. When the shield is configured as a tube, the ice pack is inserted inside the tube before the device is applied to the skin.

The method can also include controlling the heat flow by adjusting the screw between the cladding and the tube. Interpenetrating sets of concentric cylinders mounted on the tube and on the cladding allow the contact surface between the tube and the cladding to be changed and the heat conductivity of the device to be altered.

DETAILED DESCRIPTION

This invention comprises an ice pack and a thermally conductive and aseptic shield. The ice pack is applied to one side of the shield and the other side of the shield is put in contact with the skin thereby cooling the skin.

One of the preferred embodiments of the invention is illustrated in FIGS. 1, 2, 3, 4 and 5. The shield is embodied as a hollow tube 1 made of a material that conducts heat well such as aluminum, copper or stainless steel (even though stainless steel does not conduct heat as well as aluminum or copper, its surface quality makes it an attractive option). This tube 1 is open at the back end 2 and is closed at the front end 3. The walls of the tube 1 are thicker in the front to promote heat conductivity from front to back. The thickness of the tube 1 can be made to increase gradually from the back end to the front end as it dovetails with the front end 3.

The front end 3 of the tube 1 is tipped with a cladding 4 made with a material such as stainless steel that combines efficient heat conductivity with the ability for having a smooth and polished surface to facilitate cleaning, to reduce germ transmission and to provide an aseptic environment for the treatment of the skin condition. "Aseptic" describes techniques aimed at keeping patients as free from hospital micro-organisms as possible and at preventing contamination of wounds and other susceptible sites by organisms that could cause infection.

A thermal insulation layer 5, cylindrical in shape covering the outer wall of the tube 1. This layer can be made, for example, of material such as an air gel or Styrofoam®.

An outer layer 6, cylindrical in shape, covering the thermal insulation layer 5. This layer can be made, for example, of material such as plastic or rubber or a combination of these to provide the device with a desired look and feel.

In a first version of this invention, the removable ice pack 7 is comprised an essentially cylindrical soft-walled bag filled with water or a solution having a high heat of fusion and capable of being frozen into slush rather than into a hard solid. The advantage of the soft-wall bag and soft slush is that the ice pack can conform to the inside of the tube 1. A back plate 9 comprising an insulation layer 10 and a mechanically supporting layer 11 is attached to the back end of this ice pack 7 to provide insulation when the ice pack 7 is inserted into the tube 1. A handle 8 is affixed to the supporting layer 11 to facilitate the retrieval of the ice pack after it is inserted in the tube 1.

The back plate 9 can include a screw type or latch type attaching device, with the complementary screw or latch being carried by the back end 2 of the tube 1.

The solution inside the ice pack can be a slush when frozen to allow it to conform itself to the shape of the tube 1 when inserted into it. The solution may comprise any ratio of water to solute optimized for desired mechanical properties when frozen. Possible solutes include but are not limited to alcohol, superabsorbent polymer (such as Ever-Cold® gel produced by ColdIce, Inc.) and propylene glycol.

Superabsorbent polymers (SAP) (also called slush powder) are classified as hydrogels. They are polymers that can absorb and retain extremely large amounts of aqueous solutions through hydrogen bonding with the water molecule.

A typical proportion might consist of 66% water and 34% alcohol. The greater the proportion of alcohol the softer the mixture will be when frozen. In addition to freezable solutions, it is also possible to construct disposable ice packs that comprise two compartments separated by an internal barrier that, when broken through a simple squeeze or snap, permits the contents in each compartment to come into contact and generate an endothermic reaction, as demonstrated by the Instant Cold Pack produced by Dynarex. A well-known example of such an endothermic reaction would include ammonium nitrate and water.

Figure 4:
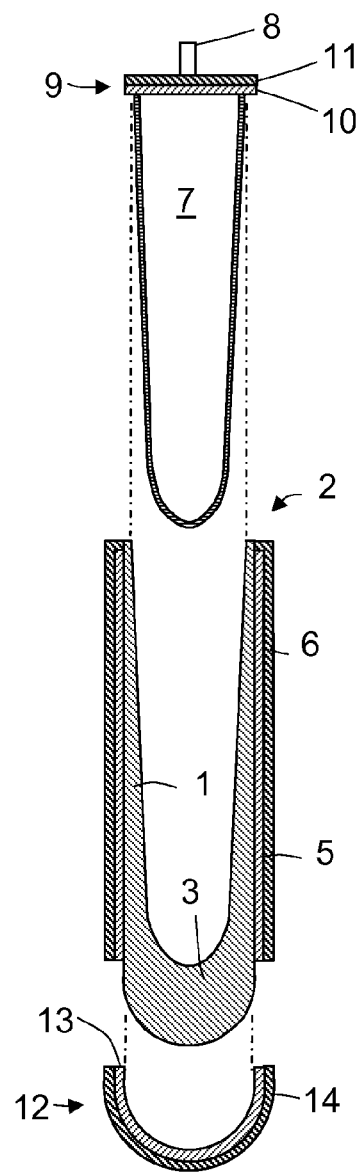
FIG. 4 illustrates a cross section and exploded version of the device in which the tip is eliminated by merging it with the tube.
Figure 5:
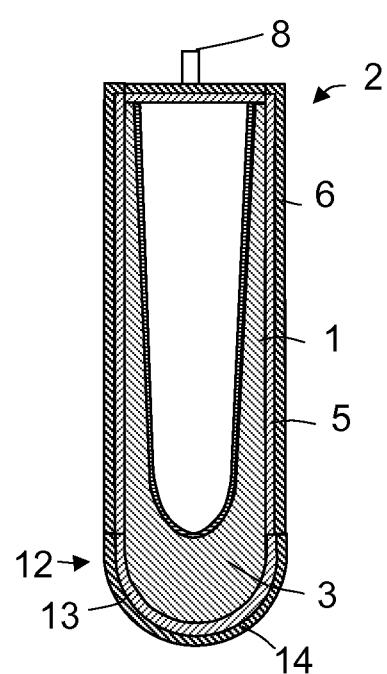
FIG. 5 shows a fully assembled view of the device in which the tip is eliminated by merging it with the tube.

In a second version of the invention shown in FIGS. 4 and 5, the removable ice pack 7 comprises a hard-wall container conforming to the inside shape of the tube 1. The icepack 7 is filled with a solution having a high heat of fusion. Care must be taken not to fill the ice-pack completely, to allow for the expansion of the solution as it freezes. Since the frozen solution does not have to be as soft as the first version, a smaller proportion of alcohol may be used, or the solution may comprise a polymer-based gel such as the previously mentioned EverCold® gel produced by ColdIce, Inc.

As is known to those familiar with the art, there are a number of other ingredients which can be used to make the ice-pack solutions. These ingredients include but are not limited to guar gum and salt. Dyes can also be used to color the ice pack mixture.

Figure 2:
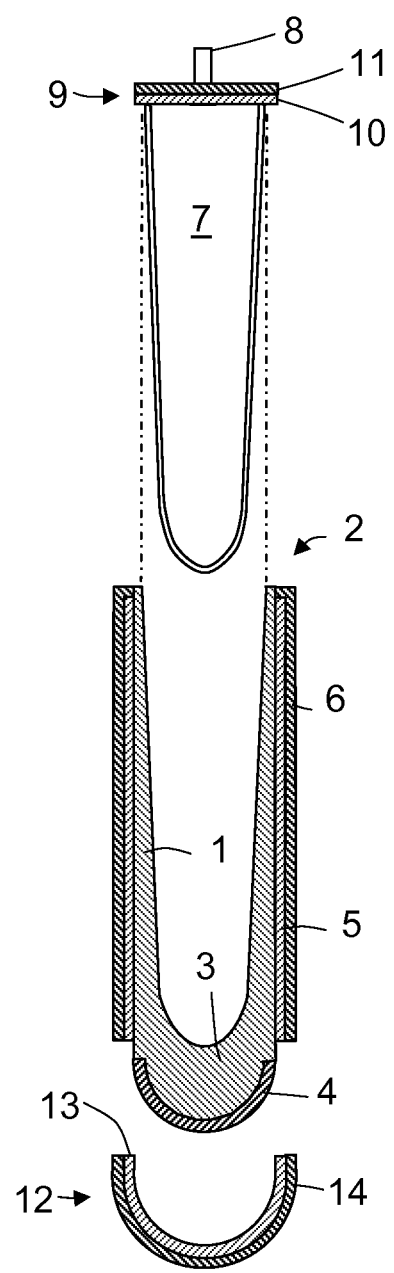
FIG. 2 provides a cross-section view of the exploded device showing the device's layers including the tube, the insulation layer, the top layer and the tip. It also shows the ice pack and the cover.
Figure 3:
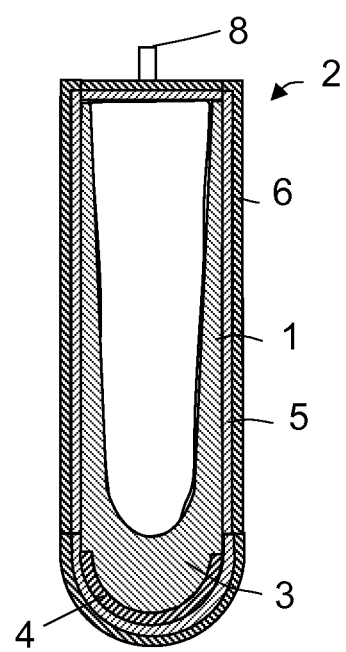
FIG. 3 shows a cross-section view of the device in a fully assembled state.

In yet another version of the invention illustrated in FIGS. 4, and 5, the tube is constructed of stainless steel, thereby voiding the need to have a separate cladding 4 (as shown in FIG. 2) at the tip of the tube.

The device also comprises a cap 12 that includes an insulation layer 13 and a mechanically supporting top layer 14. This cap 12 is configured to fit over the front end 3 of the tube 1 and the stainless steel cladding 4. It can be screwed on or snapped on.

A locking or snap mechanism may also be included and configured to maintain the ice pack 7 snugly inside the tube 1.

Figure 6:
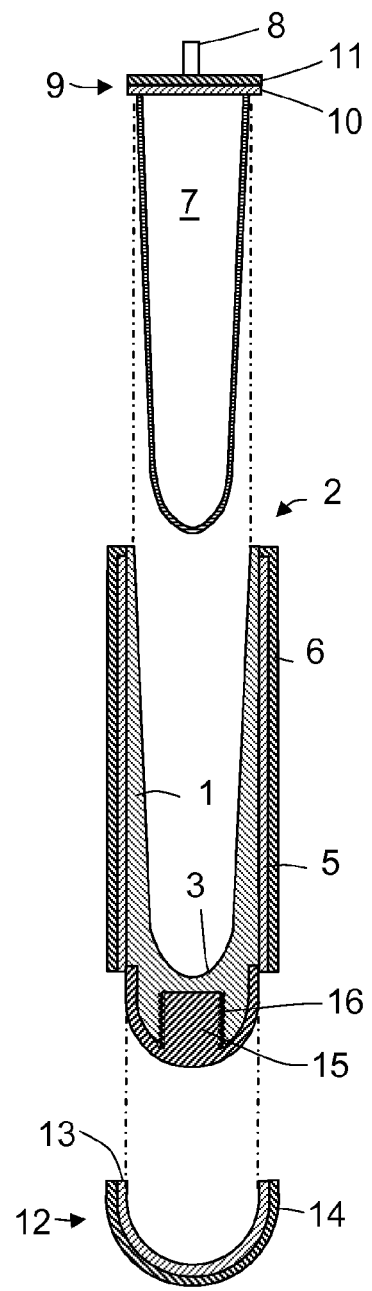
FIG. 6 illustrates the heat flow control mechanism consisting of a screw type arrangement that allows the user to vary the amount of surface area between the cladding and the tube. This figure shows the maximum contact possible.
Figure 7:
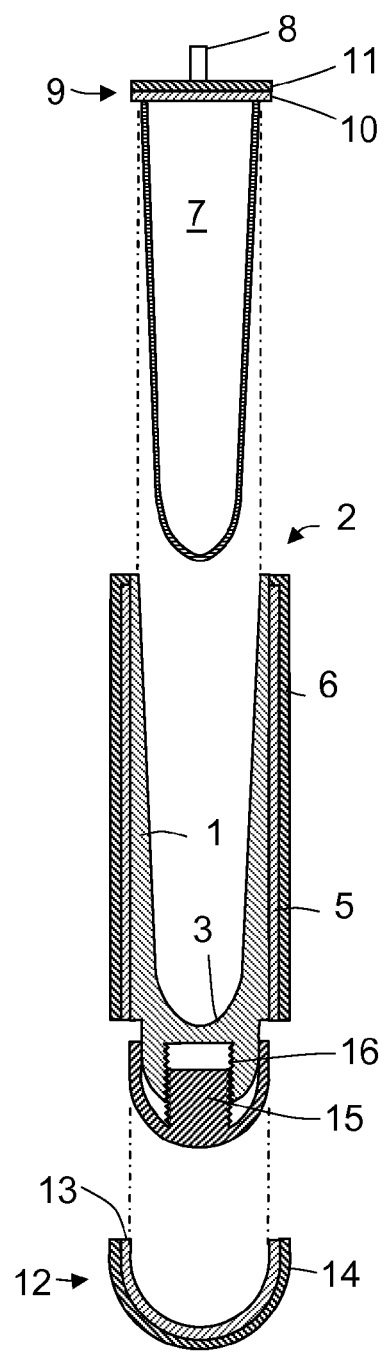
FIG. 7 illustrates the heat flow control mechanism consisting of a screw type arrangement that allows the user to vary the amount of surface area between the cladding and the tube. This figure shows an intermediate heat configuration.
Figure 8:
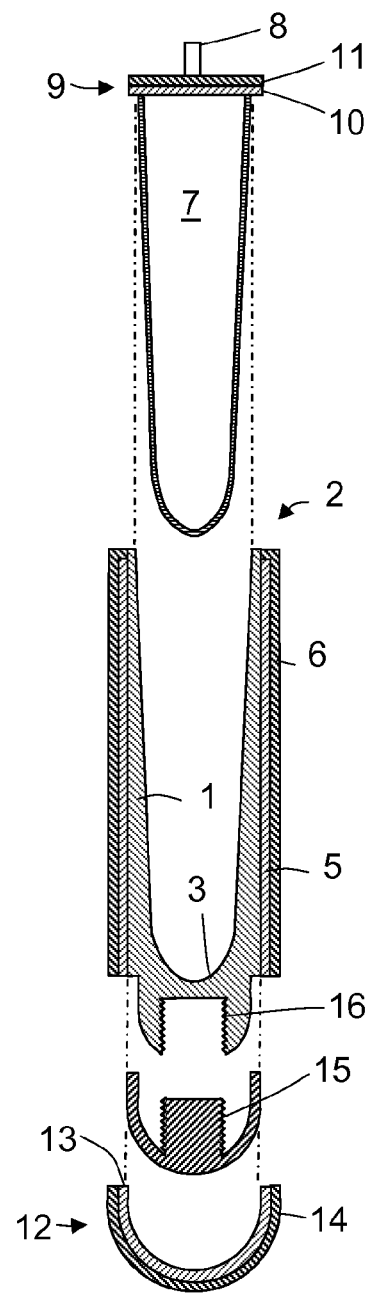
FIG. 8 illustrates the heat flow control mechanism consisting of a screw type arrangement that allows the user to vary the amount of surface area between the cladding and the tube. This figure shows an exploded view of the device.

In another version of the device, the shield is configured to have a controllable heat conductivity to allow the user to apply the amount of cold as he desires. Heat transmission can be implemented by varying the contact surface between the cladding and the tube. There are several techniques for achieving this result. One possible approach is shown in FIGS. 6, 7 and 8. The cladding 4 is mounted on a screw 15 that fits into a threaded opening 16 configured at the front end of the tube 3. The amount of contact between the cladding 4 and the tube 3 and, therefore, the heat transmission of the device, can be controlled by screwing the cladding in or out the tube.

Heat transmission control can also be implemented by providing the user with several claddings, each cladding having a different inherent heat transmission characteristic.

Figure 9:
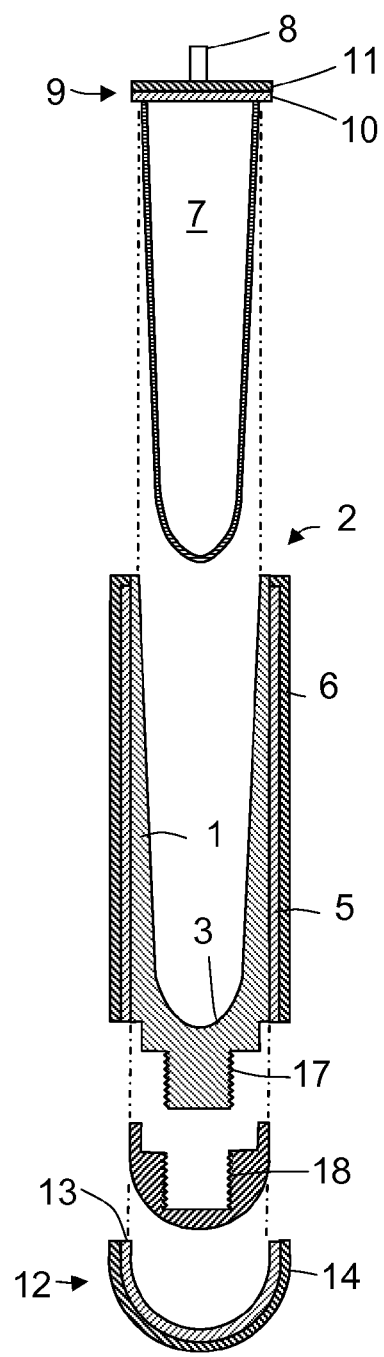
FIG. 9 shows a reversal in the sex of the screw and threaded opening that allows the cladding to be mounted on the tube.

FIG. 9 illustrates a version wherein the screw 17 is mounted on the tube and the threaded opening 18 is mounted on the cladding 4.

Figure 10:
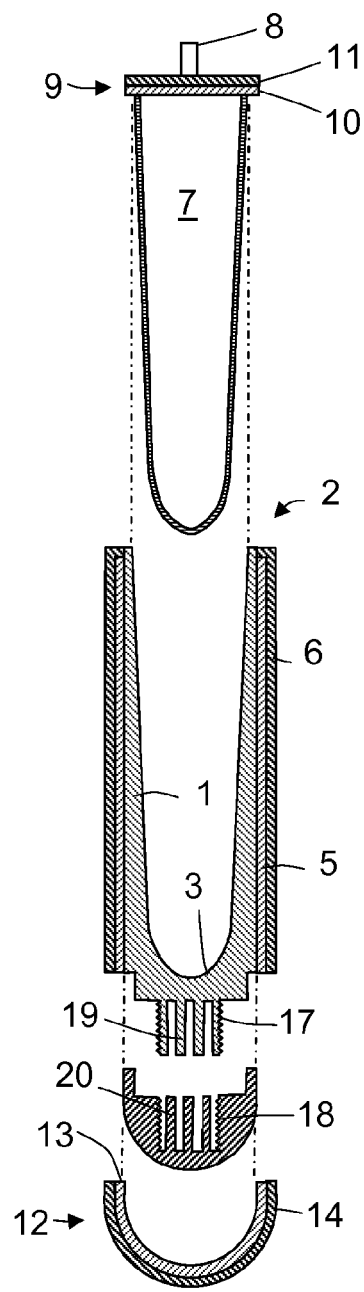
FIG. 10 illustrates how the heat conductivity of the device can be gradually altered by sliding concentric cylinders arranged in the top of the tube into a matching set of concentric cylinders in the cladding part of the device.

FIG. 10 illustrates how the heat conductivity of the device can be gradually altered by configuring the top of the tube as concentric cylinders 19 that slidingly fit into concentric cylinders 20 configured in the cladding part 4.

Operation of the Device: To use this invention, the ice pack 7 is first placed in the freezer for several hours to allow its content to freeze. The ice pack is then snugly inserted inside the tube 1 thus making firm contact with the tube 1. The insulator layers 5, 10 and 13 restrict heat flow and allow the device to remain operable over an extended period of time, typically 1 to 4 hours. The duration of cooling is influenced by external conditions, including ambient temperature, skin temperature, amount of usage, and the starting temperature of the ice pack. To use the device, the cap 12 is removed and the stainless tip 4 of the device is wiped and/or cleaned with a disinfectant. The stainless steel cladding 4 at the tip of the device is cold and can be applied to the skin to obtain the therapeutic or cosmetic effects such as reduction of swelling and redness as may occur on skin of acne sufferers.

Variations. It is clear to persons having ordinary skill in the art, that many variations are possible under the basic theme of this invention. These are some possible variations:
a) The thickness of the tube 1 can be maintained constant as it progresses from the rear to the front. This can reduce manufacturing costs.
b) The outer layer 6 could be omitted to reduce manufacturing costs.
c) The cross-sectional shape of the tubes does not have to be circular. For example it could be oval or polygonal. The tip may be pyramidal with a rounded tip in order to decrease irritation to the surrounding skin.
d) The stainless steel cladding 4 could be omitted leaving the tube 1 metal (Aluminum for example) making direct contact with the skin again to reduce manufacturing costs.
e) The stainless steel cladding 4 could be omitted by constructing the tube 1 out of stainless steel for example.

While the above description contains many specificities, the reader should not construe these as limitations on the scope of the invention, but merely as exemplifications of preferred embodiments thereof. Those skilled in the art will envision many other possible variations within its scope. Accordingly, the reader is requested to determine the scope of the invention by the appended claims and their legal equivalents, and not by the examples which have been given.

I claim:
1. A dermatological device for cooling the skin comprised of:
   a) an ice pack;
   b) a solid heat conductive shield configured to operate as an aseptic separator between said skin and said ice pack and to conduct heat from said skin to said ice pack;
   c) said shield is configured as a tube, open at one end and closed at other end, said open end called back end and said closed end called front end;
   d) said ice pack comprising a container configured to fit removably inside said tube, and be in contact with the inner surface of said tube, thereby cooling said tube; and
   e) said dermatological device also comprising a cladding, furthermore, wherein said tube is configured to have a first set of concentric cylinders and said cladding configured to have a second set of concentric cylinders, said first set of cylinders and said second set of cylinders dimensioned to slide into each other thereby allowing the amount of surface area between them to be varied and the heat transmissivity of the device to be changed.

2. The dermatological device of claim 1 wherein said tube is covered at its front end by a stainless steel cladding.

3. The dermatological device of claim 1 wherein the thickness of said tube is tapered, being thick at said front end and thin at said back end.

4. The dermatological device of claim 1 wherein said tube comprises aluminum.

5. The dermatological device of claim 1 wherein said tube comprises copper.

6. The dermatological device of claim 1 wherein said tube comprises stainless steel.

7. The dermatological device of claim 1 wherein said tube is covered on its outside surface with a thermal insulation layer.

8. The dermatological device of claim 1 also comprising a thermally insulating cap configured to fit over said front end of said tube.

9. The dermatological device of claim 1 wherein said container of said ice pack is a soft-walled bag, said bag being filled with a frozen slush.

10. The dermatological device of claim 9 wherein said slush comprises chemicals selected from the group consisting of water, alcohol and propylene glycol.

11. The dermatological device of claim 9 wherein said slush comprises superabsorbent polymers.

12. The dermatological device of claim 1 wherein said container of said ice pack has hard walls.

13. The dermatological device of claim 1 wherein said ice pack comprises a handle.

14. The dermatological device of claim 1 also comprising a locking mechanism configured to maintain said ice pack securely inside said tube.

15. A method for treating conditions of the skin utilizing dermatological device of claim 1 comprising:
   a) cooling said ice pack;
   b) applying a heat conductive shield over said skin;
   c) applying said ice pack over said shield.

16. The method of claim 15 wherein cooling of said ice pack comprises placing said ice pack in a freezer until the content of said ice pack is frozen.

17. The method of claim 15 also comprising cleaning or disinfecting said shield.

18. The method of claim 15 wherein said shield is configured as a tube having heat conductive walls, said tube being open at one end and closed at other end; said ice pack being configured to fit removably inside said tube, and be in contact with the inner surface of said tube, thereby cooling said tube, and furthermore, wherein said method of applying said ice pack over said shield also comprises inserting said ice pack into said tube.

19. The method of claim 15 wherein said shield is configured to have a controllable heat conductivity, wherein said method also comprises adjusting said heat conductivity.

* * * * *